United States Patent [19]
Lin

[11] Patent Number: 5,833,595
[45] Date of Patent: Nov. 10, 1998

[54] TREATMENT OF EXCRETORY PROBLEMS

[76] Inventor: Vernon Wen-Hau Lin, 1620 Albatross, Sunnyvale, Calif. 94087

[21] Appl. No.: 301,904

[22] Filed: Sep. 6, 1994

[51] Int. Cl.$^6$ .......................................................... A61F 2/00
[52] U.S. Cl. ..................................... 600/29; 128/DIG. 25; 607/41
[58] Field of Search .................................... 600/9, 13–15, 600/29–32; 128/DIG. 25; 607/3, 40, 41, 103, 133, 138

[56] References Cited

U.S. PATENT DOCUMENTS

| | | | |
|---|---|---|---|
| 5,190,036 | 3/1993 | Linder ...................................... | 128/421 |
| 5,314,454 | 5/1994 | Jaeger et al. ............................... | 607/62 |

OTHER PUBLICATIONS

Sacral Anterior Root Stimulation of the Bladder in *Paraolegics Anat. N.Z.J. Surg.* 1986, 56, 119–124 Arnold.

Li, et al, Role of Electric Stimulation in Bladder Evacuation Following Spinal Cord Transection *The Journal of Urology* vol. 147, 1429–1434.

Madersvacher, Intravesical Electrical Stimulation for the Rehabilitation of the Neuropathic Bladder, *Paraplegia* 28 (1990) 349–352.

Neshold et al, Electro Micturition in *Paraplegia Arch Surg* vol., Feb 1972.

Sacral Anterior Root Stimulators for Bladder Control in Paraplegia, Brindley, et al. *Paraplegia* 30 (1982) 365–38.

A Technique for Anodally Blocking Large Nerve Fibres Through Chronically Implanted Electrodes by Brindley, et al *Journal of Neurology, Neural Surgery and Psychiary* 1980, 43, 1083–1090 (hereinafter Brindley II).

Mouchawar, Closed–Chest Cardiac Stimulation with a Pulsed Magnetic Field, *Medical & Biological Engineering & Computing* Mar. 1992, p. 162.

Voorhees III et al, *Journal of Clinical Engineering* Sep./Oct. 1990 p. 407 article entitled Magnetically Induced Contraction of the Inspiratory Muscles in Dog.

Cadwell Laboratories, Inc. in Application Notes AP–2 Rev. 1 Feb. 22, 1990.

Bourland et al *IFMBE,* pp. 106–108 (Mar., 1990), Transchest Magnetic (eddy–current) stimulation of the dog heart as reported in Med. & Biol. Eng. & Comput., 1990, 28, 196–198.

IEE *Transactions on Biomedical Engineering,* vol. 37, No. 6, 1990 A Model of the Stimulation of a Nerve Fiber by Electromagnetic Induction Roth et al .

Alexander, et al, *British Journal of Urology* (1970), 42, 184–190 Treatment of Urinary Incontinence by Electric Pessary a Report of 18 Patients.

Developing a More Focal Magnetic Stimulator Part I: Some Basic Principals by Cohen et al, as recorded in *Journal of Clinical Neurophysiology,* 8(1); 102–111 (1991).

Yunokuchi et al *Journal of Clinical Neurophysiology,* 8(1); 112–120 (1991) Developing a More Focal Magnetic Stimulator. Part II: Fabricating Coils and Measuring Induced Current Distributions.

*Magnetic Stimulation in Clinical Neurophysiology* edited by Sudhansu Chokroverty and published by Butterworths, Boston, London, Singapore, Sydney, Toronto, and Wellington Chapter 3 pp. 17–32, pages showing Figures 7–18, 14–1; 17–4, 17–10, 18–3 and 18–4.

*Magnetic Brain Stimulation With a Double–Coil: The importance of Coil Orientation* by Mills et al. published in Electroencephalography and Clinical Neurophysiology, 85 (1992) pp. 17–21.

(List continued on next page.)

Primary Examiner—Angela D. Sykes
Assistant Examiner—John P. Lacyk
Attorney, Agent, or Firm—F. L. Collins

[57] ABSTRACT

This invention deals with inducing urination and/or defecation through electro-magnetic induction. The claimed method provides a non-invasive procedure to stimulate excretory functions in paraplegic and quadriplegic patients.

24 Claims, 4 Drawing Sheets

OTHER PUBLICATIONS

*Effects of Coil Design on Delivery of Focal Magnetic Stimulation–Technical Considerations* Cohen et al.

Electroencephalography and Clinical Neurophysiology, 75 (1990) pp. 350–357.

Brodak et al. *Magnetic Stimulation of Sacral Roots* Neurology and Urodynamics 12: pp. 533–540 (1993).

*Motor Evoked Potentials From the Bladder on Magnetic Stimulation of the Cauda Equina: New Techniques for Investigation of Autonomic Bladder Innervation* Journal of Urology 147: pp. 658–661 (1992).

Oct. 8, 1993 Annual meeting of the AAEM Annual Meeting *High Frequency Magnetic Stimulation of the Inspiratory Muscles* Oral presentation by the applicant.

AAEM Annual Meeting Oct. 8, 1993 *Magnetic Stimulation of the Bladder in Dogs* Oral presentation by the applicant.

TREATMENT OF EXCRETORY PROBLEMS

BACKGROUND OF THE INVENTION

1. Field of the Invention

This invention deals with the treatment of excretory functions including urinary and defecation problems in mammals wherein the normal function is absent or severely impaired.

2. Description of the Art Practices

It is known for most paraplegics that the bladder empties automatically and necessitates the wearing of an external collecting device. Reflex bladder contractions occur where the urethral sphincter may undergo an intermittent spastic contraction interrupting voiding and frequently leading to high bladder pressures. The foregoing situation is also accompanied by incomplete bladder emptying also known as detrusor sphincter-dyssynergia.

Typically, a patient whose sacral cord, or cauda equina is damaged often results in a flaccid bladder. Intermittent self catheterization is often used by patients who are unable to completely void the bladder thus leaving a large residual amount of urine which predisposes the urinary tract to infections.

In addition to patients with spinal injuries, there is also the situation of surgical patients who need to void their bladder. The micturition process in patients under anesthesia may be necessary to prevent abnormally high bladder pressure. Such situation occurs where the patient is in need of urgent surgery, and normal procedures for bladder evacuation must be deferred. Another situation in which micturition may benefit from controlled response is in geriatric patients. In such situations it may be necessary to stimulate the patients bladder in a controlled setting to avoid bed wetting.

Arnold, et al. discusses bladder function in an article entitled Sacral Anterior Root Stimulation of the Bladder in *Paraplegics Aust. N.Z.J. Surg.* 1986, 56, 119–124. The Arnold article treats the treatment of patients 12 month post-injury to allow the neurological status to become stable. Arnold describes the patient as being positioned in a prone situation and laminectomies of L3 to S2 (inclusive) are performed. The dura is then opened in the mid-line at the L4/L5 level to S2 with initial anatomical localization of the cauda equina nerves. Commencing unilaterally, the S 2 nerves are then identified and the motor and sensory components separated. Direct nerve stimulation is performed on the motor and sensory components with observation made of the detrusor and rectal pressures, pelvic floor and distal limb muscles.

The second stage of the operation in Arnold's patient is performed a week later. The patient is positioned in the lateral decubitus position and the coiled cables in the cutaneous pouch are exposed and lead subcutaneously to a radial-receiver unit which is placed in a subcutaneous pouch over the anterial lateral chest wall over ribs.

The transmitter coils are connected by a short cable to the signal generator control box which allows adjustment of the strength and frequency, shape and timing of the desired electro-stimulation. It is observed that voiding occurs in spurts after each burst of stimulation. The procedure of Arnold is difficult to put in practice with only two-thirds of the patients initially indicating a satisfactory response following surgery.

Li, et al, in Role of Electric Stimulation in Bladder Evacuation Following Spinal Cord Transection discusses bladder stimulation in *The Journal of Urology* vol. 147, 1429–1434. Li teaches neural stimulation as a potentially valuable therapeutic tool in the treatment of neurogenic bladder with detrusor areflexia.

Li discloses that the urinary bladder receives its innervation from 3 sources: Somatic, Sympathetic, and Para-Sympathetic. The Sympathetic innervation of the bladder is controlled by the hypogastric nerve; para-sympathetic impulses are carried by the pelvic nerve. The pudendal nerve which is derived from the sacral nerves supplies somatic innervation to the striated musculature of the urethra. Li notes that the Somatic and Autonomic reflexes are lost in the event of a spinal cord lesion.

A review article was released by Madersvacher entitled Intravesical Electrical Stimulation for the Rehabilitation of the Neuropathic Bladder, *Paraplegia* 28 (1990) 349–352. Madersvacher stated that introvesical electro-stimulation dates back to 1878 which Saxtroph treated urinary retention by inserting a special catheter trans-uretherally into the bladder with a metal-electrode inside and with a neutral electrode placed supra-pubically. The idea of electro-stimulation of the bladder to encourage functional micturition laid dormant until 1959 when Katona et al described the technique of intraluminal electro-therapy. Madersvacher also discusses trans-urethral electro-stimulation of the bladder being based on the activation of specific receptors in the bladder wall.

Nashold et al, in Electro Micturition, in *Paraplegia Arch Surg* Vol., February 1972. Nashold describes a paraplegic patients who have undergone electrode implantation in the S1–S2 region of the conus mudullaris. The electro-stimulation proceeded with a small battery-operated radio frequency stimulator and the receiver is stated to produce adequate emptying of the bladder every 3 to 4 hours. The male patients were stated to have required a sphincterotomy. Nashold states that the stimulation indexes employed at surgery and during the initial testing were biphasic square wave ranging from 100 to 500 microseconds in duration at various frequencies and voltages. Specific data concerning the parameters of Nashold indicate that the patient at home uses stimulation indexes of 15 to 30 cycles per second, 10 to 15 volts and 200 micro-second pulses for 30 to 60 seconds for emptying the bladder.

Urinary stimulation is discussed in an article entitled Sacral Anterior Root Stimulators for Bladder Control in Paraplegia by Brindley, et al. reported at *Paraplegia* 30 (1982) 365–381. Brindley discloses that patients whose bladders remain innervated by an isolated cord that is not severely damaged can achieve reflex micturition. However, many of the patients according to Brindley have large residual urine volumes and suffer from a persistently or recurringly infected urine.

Brindley discusses an implant consisting of three parts. The Brindley article discusses the use of electrode "books" in which the sacral roots are trapped with three electrodes in each slot. Brindley discusses avoiding pressure through a thin urethral catheter during implant driven micturition after the implants had been in use for several months.

The discussion of chronically implanted electrodes for treatment of the spinal root is discussed in A Technique for Anodally Blocking Large Nerve Fibres Through Chronically Implanted Electrodes by Brindley, et al *Journal of Neurology Neural Surgery and Psychiatry* 1980, 43, 1083–1090 (hereinafter Brindley II).

Mouchawar, in an article entitled Closed-Chest Cardiac Stimulation with a Pulsed Magnetic Field, *Medical & Biological Engineering & Computing* March 1992, page 162 discusses magnetic stimulator to generate intense, rapidly changing magnetic fields capable of stimulating nerves. Magnetic resonance systems utilizing coplanar coils to provide a pulsed magnetic field with an average of 12 kilojoules to achieve closed-chest magnetically induced ectopic beats. The Mouchawar article also describes the peak-induced electrical field for threshold stimulation at 213 V/m for a 571 micro-second damped sine wave pulse.

Voorhees III et al, in a technical note in the *Journal of Clinical Engineering* September/October 1990 page 407 article entitled Magnetically Induced Contraction of the Inspiratory Muscles in Dog discusses short-duration inspirations by discharging a capacitor bank into an excitation coil placed over the lower right chest. The Voorhees III article discusses utilizing the construction of the excitation coil as having 59 turns of ¼ inch copper ribbon 0.0200 inches thick wound on a ¾" diameter plastic rod where the outer diameter of the coil is 3.75" and the entire coil is potted in silicon rubber.

The inductance per Voorhees III et al is 139 micro-H and the resistance is 0.084 ohms. The current was delivered to the coil from a 100-micro F capacitor bank. The resonant frequency of the system was 1350 Hz and the damping coefficient was 0.05.

Cadwell Laboratories, Inc. in Application Notes AP-2 Rev. 1 Feb. 22, 1990, discusses high speed magnetic stimulator characteristics. In a technical note by Bourland et al in *IFMBE*, page 106–108 (March, 1990), entitled Transchest Magnetic (eddy-current) stimulation of the dog heart as reported in Med. & Biol. Eng. & Comput., 1990, 28, 196–198. The magnetic stimulator used by Bourland et al is described as a pulse generator with two coplanar coils connected in a series so that the current flows in a clock-wise direction in one coil and counter-clockwise in the other.

The Bourland et al coil and generator specifications were stated to be determined from computer simulations, and were optimized for minimal energy stored in the generator. The coils were described as 30-turn 106 Micro H Coil fabricated from ½" by 0.043" copper ribbon covered with a glass-epoxy insulation. The inter-diameter of each coil is 7.2 cm and the outer diameter is 16.5 cm. The magnetic stimulator and coils is a series RLC circuit, comprising a 682 micro F, 9900 V Capacitor, output switch (ignition) and 220 micro H inductor (combined value for both coils, including mutual inductance). The resistance of the Bourland device is stated to be 220 m ohms and a reverse-biased diode is connected across the 682 micro-capacitor to prevent reverse polarization.

A discussion of nerve stimulation was presented in IEE *Transactions on Biomedical Engineering*, Volume 37, NO. 6, 1990 under the heading of A Model of the Stimulation of a Nerve Fiber by Electromagnetic Induction by Roth et al.

Alexander, et al, in *British Journal of Urology* (1970), 42, 184–190 discusses electric pessary stimulation in a paper entitled Treatment of Urinary Incontinence by Electric Pessary A Report of 18 Patients.

In an article entitled Developing a More Focal Magnetic Stimulator Part I: Some Basic Principals by Cohen et al, as recorded in *Journal of Clinical Neurophysiology,* 8 (1); 102–111 (1991) magnetic stimulation is discussed generally. Similar disclosures are made by Yunokuchi et al in the *Journal of Clinical Neurophysiology,* 8 (1); 112–120 (1991) in an article entitled Developing a More Focal Magnetic Stimulator. Part II: Fabricating Coils and Measuring Induced Current Distributions.

The reader is also referred to *Magnetic Stimulation in Clinical Neurophysiology* edited by Sudhansu Chokroverty and published by Butterworths, Boston, London, Singapore, Sydney, Toronto, and Wellington Chapter 3 pages 17 through 32, pages showing FIGS. 7-18; 14-1; 17-4; 17-10, 18-3 and 18-4.

Further reference is made to *Magnetic Brain Stimulation With a Double Coil: The importance of Coil Orientation* by Mills et al. published in Electroencephalography and Clinical Neurophysiology, 85 (1992) pages 17–21. Reference is also made to a publication entitled the *Effects of Coil Design on Delivery of Focal Magnetic Stimulation-Technical Considerations* Cohen et al. Electroencephalography and Clinical Neurophysiology, 75 (1990) pages 350–357.

Further reading on the subject of magnetic studies of mammals is found in Brodak et al. *Magnetic Stimulation of Sacral Roots* Neurology and Urodynamics 12: pages 533–540 (1993) and in *Motor Evoked Potentials From the Bladder on Magnetic Stimulation of the Cauda Equina: New Techniques for Investigation of Autonomic Bladder Innervation* published in the Journal of Urology 147: pages 658–661 (1992).

A summary of the results of the magnetic stimulation presented in this patent was made on Oct. 8, 1993 at the annual meeting of the AAEM Annual Meeting under the heading of *High Frequency Magnetic Stimulation of the Inspiratory Muscles.* A second presentation to the AAEM Annual Meeting on Oct. 8, 1993 concerned *Magnetic Stimulation of the Bladder in Dogs.*

To the extent that the foregoing references are relevant to the present invention, they are herein specifically incorporated by reference. Where temperatures are given, they are in degrees C unless otherwise indicated. Pressure measurements are reported with reference to the reading at pubic symphysis as zero. Percentages and ratios given herein are by weight unless otherwise indicated. Measurements herein are stated in degrees of approximation thereby where appropriate the word "about" may be indicated before any measurement.

SUMMARY OF THE INVENTION

The present invention is directed to a method for treating a mammalian subject to regulate the excretory function including the steps of exposing the subject to sufficient electro-magnetic induction for a sufficient period of time to induce the excretory function.

The present invention also provides a method for treating a mammalian subject to regulate the urinary function including the steps of exposing the subject to sufficient electro-magnetic induction for a sufficient period of time to induce the excretory function wherein the field strength maximum is less than 5.0 Tesla, and having a focus of the electro-magnetic induction including that portion of the anatomy of the mammalian subject between the L1 and S5 vertebrae, and provided further that the pressure of the urinary bladder is measured prior to and/or during the electro-magnetic induction.

DETAILED DESCRIPTION OF THE DRAWINGS

Figure 1:
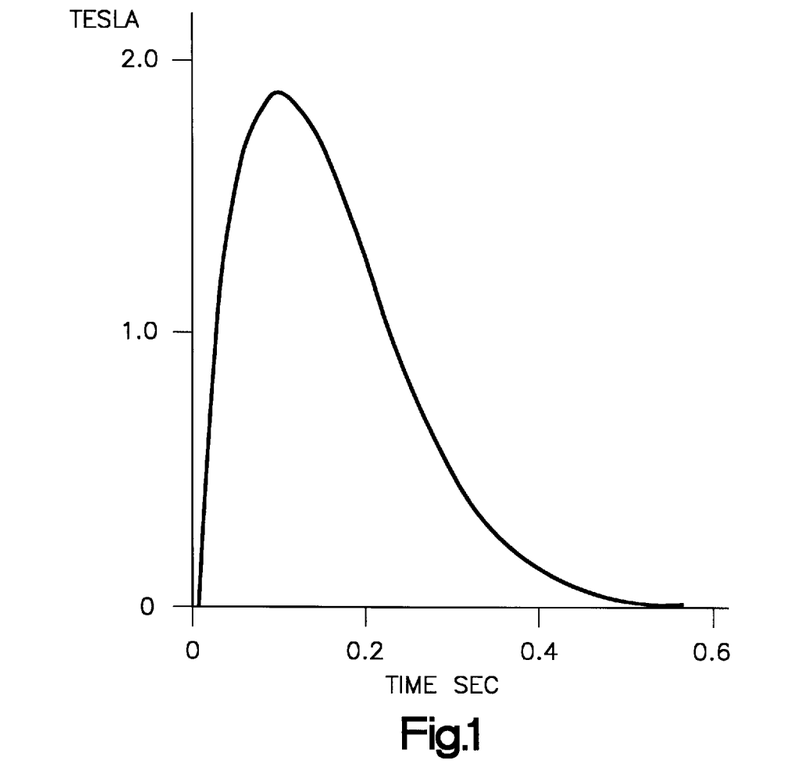
FIG. 1 is a graph of the magnetic field at the center of a 70-mm mean diameter stimulation coil.

With more particular reference to the drawings the following is set forth. FIG. 1 is self explanatory showing the relationship of a magnetic field at the center of a 70-mm mean diameter stimulation coil such as may be employed in the present invention.

Figure 2:
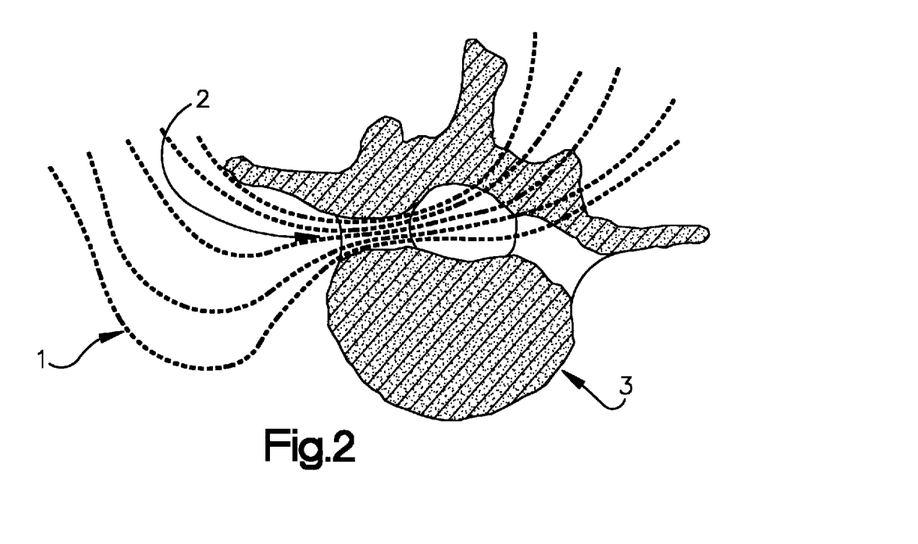
FIG. 2 shows current focusing at a vertebral foramen.

FIG. 2 shows magnetic current 1 focusing at a vertebral foramen 2 (orifice in the bony structure of the vertebra 3).

Figure 3:
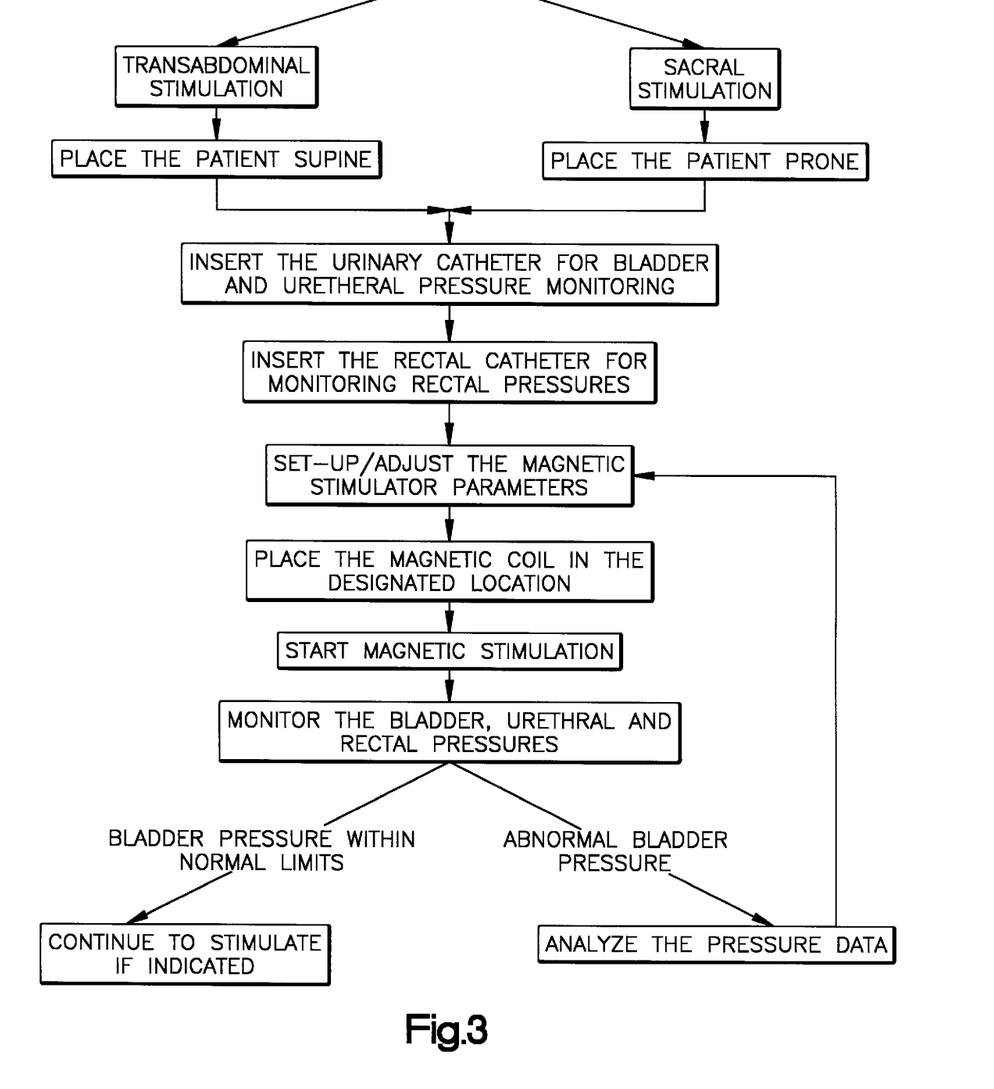
FIG. 3 shows a flow chart for determining the protocol to be used on a selected subject.

FIG. 3 is a flow chart for determining the protocol to be used on a selected subject depending upon whether transabdominal and supine, or sacral and prone electro-magnetic induction stimulation is desired.

Figure 4:
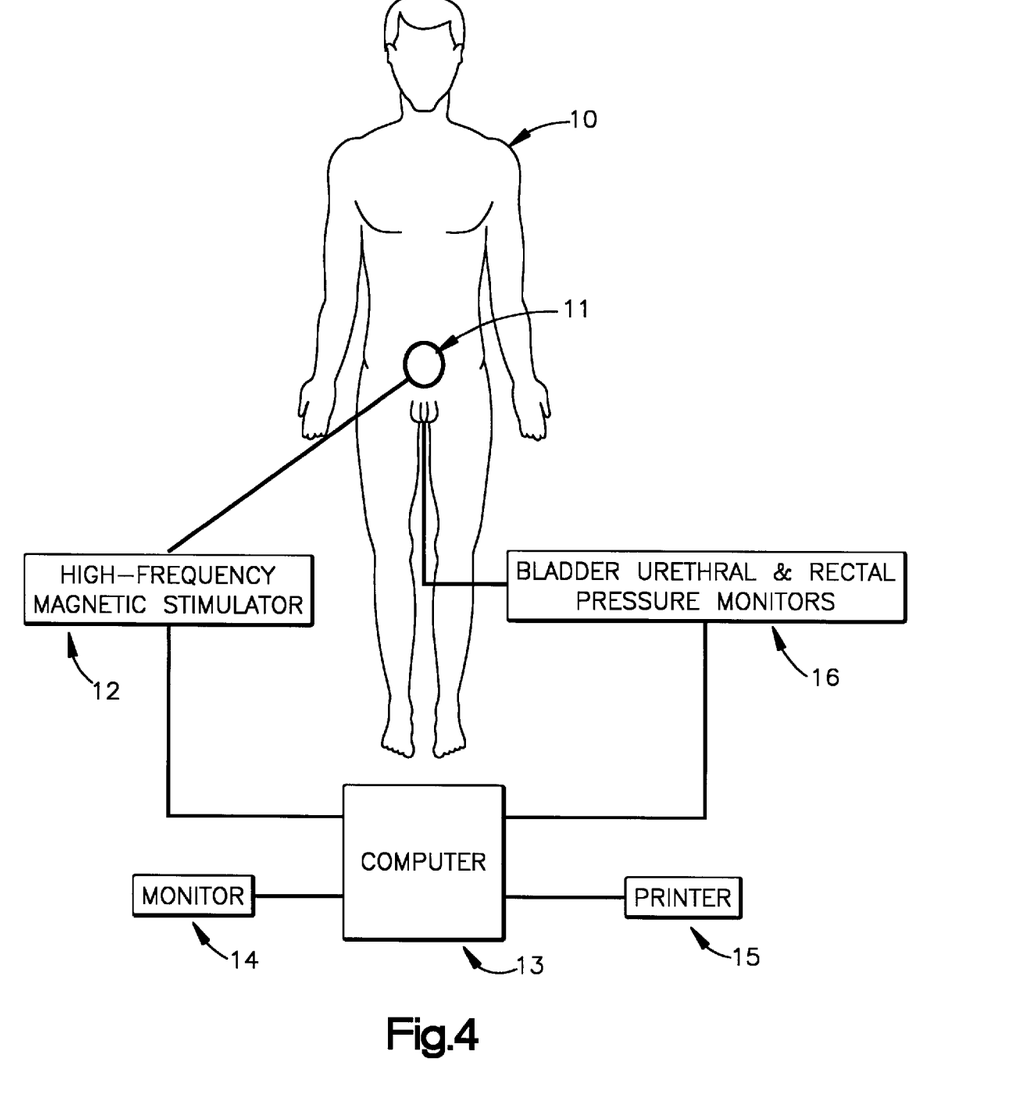
FIG. 4 shows a male subject with anterior placement of the magnetic coil with various systemic functions being measured.

FIG. 4 shows a male 10 subject with anterior placement of the magnetic coil 11 with a electro-magnetic stimulation provided by 12 a high frequency magnetic stimulator driven by a computer 13 with monitor 14 and printer 15. Bladder, rectal and urethral pressure sensing devices are shown jointly as 16 and are connected to the computer 13 for monitoring, recording and feedback for measuring each function and changing the level, duration, and interval between each electro-magnetic stimulation.

Figure 5:
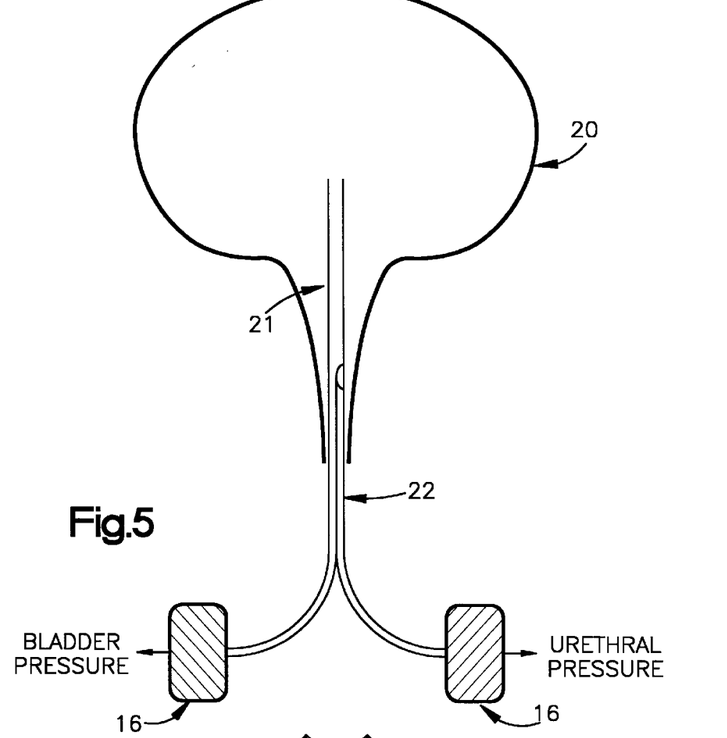
FIG. 5 shows the simulation of a mammalian bladder and urethra both of which are monitored for baseline and electromagnetically induced pressure.

FIG. 5 shows the simulation of a mammalian bladder 20 and urethra both of which are monitored for baseline and electro-magnetically induced pressure by a bladder pressure catheter 21 and a urethral pressure catheter 22 both of which feed data to computer 13 (not shown).

Figure 6:
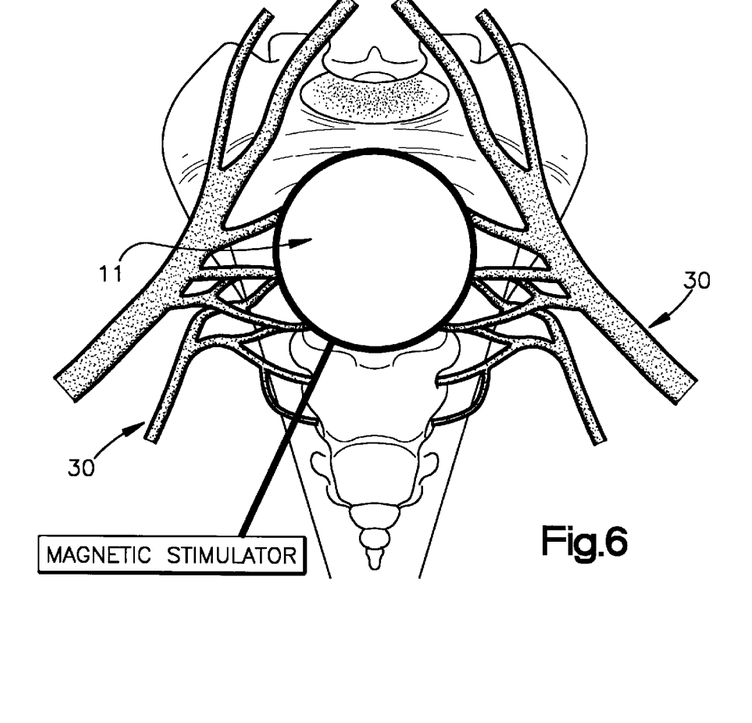
FIG. 6 shows the magnetic stimulator (source of electromagnetic induction) in relation to the sacral nerves of a subject.

FIG. 6 shows the magnetic stimulator coil 11 (source of electro-magnetic induction) in relation to the sacral nerves 30 of a subject. Each of the sacral nerves is also separately noted by number in accordance with accepted practice.

DETAILED DESCRIPTION OF THE INVENTION

As previously discussed the present invention is concerned with excretory functions. In particular, the excretory functions of mammals are primarily urination (micturition) and defecation. In this patent, the term mammals includes all mammals, particularly those which are land-dwelling, and includes humans.

In mammals, where there has been a spinal cord injury, the resulting paralysis ordinarily extends beyond the point of the injury to the extremities. In the case of the urinary function, the bladder must typically be catheterized. That is, in the absence of sufficient nerve activity to stimulate the muscles surrounding the bladder, there is no proper bladder function.

The defecation function in mammals is somewhat less sensitive to spinal injury, as the vagus nerve supplies the excitatory parasympathetic activities from the esophagus to the mid-transverse colon. With proper diet and bowel care, defecation may occur.

In either the case of urination or defecation, there is a need for nerve function below the point of the injury to void urine and feces. In addition to nerve function the bladder it self being regulated by smooth muscle tissue may be reflexive, hyper reflexive or flaccid. The method of treatment described herein is to a greater or lesser extent useful in each of the aforementioned bladder states, however, as a practical matter the hyper reflexive or flaccid states will be the primary focus of eh present invention.

Currently, hospitals periodically catheterize bladder-impaired patients. The process is costly and time-consuming, often resulting in additional trauma to the subject. Assisted defecation must be done with the process of enema or electrical stimulation of the bowel. The limited diet of a subject, the discomfort of constant enema or electrical stimulation often results in the patient giving up the will to live.

As previously discussed the invention deals with a non-physically invasive method to stimulate the urinary function and defecation function. The equipment utilized for the functional magnetic stimulation (electro-magnetic induction) of the excretory function is conveniently available as a Cadwell HS M E S-10 Magnetic Stimulator 12 which is available from Cadwell Laboratories, Inc. 909 N. Kellogg Street, Kennewick, Wash. 99336.

In any event, any suitable magnetic stimulation device may be utilized in the present invention. The general parameters for treating a mammalian subject are to expose the subject to a field strength between 1 Hertz and 150 hertz, preferably 3 Hertz to 100 Hertz and more preferably 10 Hertz to 40 Hertz. The duration of the stimulation provided is typically from 0.5 to 30 seconds, often 0.75 to 15 seconds and most preferably from 1 second to 8 seconds.

To approximate normal bladder and bowel function, the electro-magnetic induction is employed in repeated intervals from 0.5 to 20 seconds, typically 1 second to 15 seconds and most preferably 3 seconds to 12 seconds. The total number of the electro-magnetic induction cycles for urination stimulation are typically from 1 to 100, typically 2 to 50, and often 6 to 25. Desirably, the micturition will result in at least 100 milliliters, preferably at least 200 milliliters, and most preferably at least 250 milliliters of urine being voided during each episode of cycles of electro-magnetic induction, e.g. each series of treatments of the subject.

The electro-magnetic induction may be varied depending upon the patient response between each interval. Stated otherwise insufficient response in the bowel or bladder will usually require slightly greater amounts of electro-magnetic induction in each interval until the optimum has been achieved. Often, the bowel function will require greater stimulation than the urinary function.

As later discussed, the bladder of injured patients may become dangerously full between voiding. A further aspect of the invention is the monitoring of the bladder to prevent damage thereto or to the urethra. For the moment, it is safe to say that the history of the treatment of each subject may be conveniently recorded electronically with the information fed into a computer so that each patients' profile is set for optimal elimination of urine and/or feces. Once the bladder and/or urethra and/or bowel profiles (particularly pressure) have been observed the catheterization such as for pressure measurements may be discontinued or monitored only intermittently thus causing less stress and pain to the subject.

As the bladder is typically much more sensitive to stimulation and the risk of injury it will typically be observed that it is more effective to stimulate for urinary function and thereafter increasing the stimulation for bowel function. However, there is no particular difficulty in utilizing both bowel and urinary function stimulation at the same time. Of course, where there may be any subject discomfort, the appropriate electro-magnetic induction may be utilized to only induce the desired excretory function.

The subject's behavior under stimulation may be aided by utilizing well known medical devices such as X-ray and ultra sound to determine the degree of success in the electro-magnetic induction of the excretory system. Typically, the entire bladder will not need to be completely voided, but will only be voided to the extent necessary to approximate a normal excretory function.

The location of the electro-magnetic induction is such that the coil will be placed directly upon the subject, up to a distance of not more than 0.1 meter, more preferably less than 1 cm or 0.5 cm from the surface of the subject. As there is a linear effect to the electro-magnetic radiation, it is desired that the coils be placed relatively close to the subject to accomplish several purposes.

First, by placing the coil close to the subject there will be little over-spray of the electro-magnetic radiation with the avoidance of stimulating other functions, such as respiration or cardiac function. Secondly, by placing the coils relatively close to the subject, the differences in signal strength of the electro-magnetic radiation will be minimized.

Lastly, the patient profile may be adjusted for the distance from the subject during the electro-magnetic induction. In some situations, the subject may have a sensitivity to having the coils placed directly upon the body which may be either of a physiological or psychological nature. Thus, by avoiding intimate contact with the subject, some degree of comfort may be obtained by the subject.

The area of the subject to be stimulated is typically in the lumbosacral region between the L1 and S5 vertebrae. Conveniently, the electro-magnetic induction is addressed to the area between the L4 and S3 vertebrae. The subject may conveniently be either in the supine or the prone position. It is expected that with suitable experimentation a normal bowel function, while seated on the toilet may be possible.

The urinary function upon electro-magnetic induction will typically increase the bladder pressure to from 10 to 150 centimeters of water. As previously discussed the pressure of the urinary bladder may be measured in the subject before, during and after the electro-magnetic induction is initiated. A baseline may be obtained for the patient by utilizing a Dantec 5000 Urodynamic Investigation System.

A further variable in the present invention is the avoidance inducing urethra pressure with the electro-magnetic induction substantially greater than the bladder pressure which is induced. That is, it is possible to stimulate both the bladder and the urethra substantially simultaneously such that micturition does not occur. Of course, if the bladder pressure is too great harm may occur to the subject when micturition does not occur. Thus it is desirable to monitor both the bladder and urethra pressure to maintain a differential when the electro-magnetic induction is occurring such that no harm occurs to the either urinary system. Typically, the induced pressure of the bladder should be greater than that of the urethra by a factor of preferably at least 50%, preferably at least 40% and even greater than 20%.

Conveniently, the mammalian subject is exposed to a field strength maximum of less than 3.0 Tesla. Conveniently the field strength maximum is less than 5.0 Tesla. The electro-magnetic induction device is typically operated between 50% and 100% of the maximum power, conveniently 60% to 80% of the maximum power. The maximum radiation strength per cycle of the electro-magnetic induction is maintained at less than about 50 microcurie per pulse.

The following is an exemplification of the present invention:

EXAMPLE I

A laboratory dog is stimulated utilizing a 9 centimeter coil placed firmly at the supra pubic region. A 4 second train of 20 Hz magnetic stimulation at 70% output is utilized. Peak bladder pressure in the animal is observed at 114 centimeters water of which 24 centimeters of water was due to a detrusor contraction.

The animal is observed to both urinate and defecate during the procedure.

EXAMPLE II

The following example is conducted on two human volunteer patients which were paraplegic at the T-7 location.

One patient was treated by placing the magnetic coil at the suprapubic region in the supine position and the second patient was treated in the lumbar position while in the prone position. In both cases the magnetic coil was placed directly on the patient.

The first patient demonstrates spontaneous uninhibited contractions of the bladder at approximately 110 milliliters of water filling in a routine water cystometry. The treatment level is a 3-second Hz stimulation at 70% power output. The peak bladder pressure increases from 20 centimeters at the baseline to 34 centimeters of water while the rectal pressure increases from 45 to 57 centimeters of water.

While lying prone, and applying the same stimulation to the lumbar region, the bladder pressure increases from 20 to 82 centimeters of water, and the rectal pressure increases from 46 to 104 centimeters water. By repetitively stimulating the lumbosacral region it is observed that spontaneous defecation occurs.

The second paraplegic patient demonstrated a flaccid bladder at 800 millimeters of fluid filling in the water cystometry. The second patient was placed in a supine position and the bladder filled at approximately 500 milliliters of fluid. The magnetic coil was placed at the suprapubic region and a three second train of 30 Hz magnetic stimulation with 70% power output is employed.

It is observed that the peak bladder pressure increases from 24 at baseline 265 centimeters water. The rectal pressure in the second patient increases from 32 to 56 centimeters water. When lying prone, and applying the same stimulation to the lumbar region, the second patient's bladder pressure increases from 32 to 77 centimeters water, and the rectal pressure increases from 23 to 48 centimeters water. Both urination and defecation occurred by repetitively stimulating the lumbar region.

What is claimed is:

1. A method for treating a mammalian subject to regulate the urinary function including the steps of exposing the subject to sufficient electro-magnetic induction for a sufficient period of time to induce the urinary function and wherein the pressure of the urinary bladder is measured prior to and/or during the electro-magnetic induction.

2. The method of claim 1 where in the mammalian subject is human.

3. The method of claim 1 wherein the electro-magnetic induction generates a field strength and the mammalian subject is exposed to a field strength between 1 Hertz and 150 Hertz in the region below the navel and above the buttocks.

4. The method of claim 1 wherein the electromagnetic induction is focused and the focus of the electro-magnetic induction includes that portion of the anatomy of the mammalian subject between the L1 and S5 vertebrae.

5. The method of claim 4 wherein the mammalian subject is in the prone position during the electro-magnetic induction.

6. The method of claim 1 wherein the electro-magnetic induction is employed in cycles and the cycles of the electro-magnetic induction are from about 0.5 to 30 seconds.

7. The method of claim 1 wherein the electro-magnetic induction is employed in cycles and the electro-magnetic induction generates radiation such that the maximum radiation strength per cycle of the electro-magnetic induction is less than about 50 microcurie per electro-magnetic induction.

8. The method of claim 1 wherein the electro-magnetic induction generates a field strength and the field strength maximum is less than 5.0 Tesla.

9. The method of claim 1 wherein the urinary function induces an increase in the urinary bladder pressure of at least 20 centimeters of water.

10. The method of claim 1 wherein the pressure of the urinary bladder is measured substantially contemporaneously prior to and/or during the electro-magnetic induction.

11. The method of claim 12 wherein the pressure of the urinary bladder is measured during the electro-magnetic induction with the bladder pressure measurements used to adjust the electro-magnetic induction.

12. The method of claim 13 wherein the pressure of the urinary bladder is maintained at less than twice the initial pressure of the urinary bladder.

13. The method of claim 1 wherein more than one electro-magnetic induction is employed per single urinary function.

14. The method of claim 1 wherein the electromagnetic induction is focused and the focus of the electro-magnetic induction includes that portion of the anatomy of the mammalian subject between the L4 and S3 vertebrae.

15. The method of claim 1 wherein the electro-magnetic induction is employed in cycles to induce urination by the mammalian subject and the total number of the electro-magnetic induction cycles for each such induced urination are from 2 to 100 cycles.

16. The method of claim 1 wherein the electro-magnetic induction generates a field strength and the field strength maximum is less than 3.0 Tesla.

17. The method of claim 15 wherein more than one electro-magnetic induction cycle is employed per single urinary function with an interval between the electro-magnetic inductions from 0.5 to 20 seconds.

18. A method for treating a mammalian subject to regulate the urinary function including the steps of exposing the subject to sufficient electro-magnetic induction for a sufficient period of time to induce the excretory function wherein the field strength maximum is less than 5.0 Tesla, and having a focus of the electro-magnetic induction including that portion of the anatomy of the mammalian subject between the L1 and S5 vertebrae, and provided further that the pressure of the urinary bladder is measured prior to and/or during the electro-magnetic induction.

19. The method of claim 1 wherein the excretory function is the urinary function.

20. The method of claim 1 wherein the excretory function is the defecation function.

21. A method for treating a mammalian subject to regulate the defecation function including the steps of exposing the subject to sufficient electro-magnetic induction for a sufficient period of time to induce the defecation function.

22. A method for treating a human subject to stimulate the urinary function including the steps of exposing the subject to sufficient electro-magnetic induction for a sufficient period of time to induce the urinary function wherein the field strength maximum is less than 5.0 Tesla, and having a focus of the electro-magnetic induction including that portion of the anatomy of the human subject between the L1 and S5 vertebrae, and provided further that the pressure of the urinary bladder is measured prior to and/or during the electro-magnetic induction.

23. The method of claim 22 wherein the electro-magnetic induction is employed in cycles and the cycles of the electro-magnetic induction are from about 0.5 to 30 seconds.

24. The method of claim 23 wherein the electro-magnetic induction is employed in cycles to stimulate urination by the human subject and the total number of the electro-magnetic induction cycles for each such stimulated urination are from 2 to 100 cycles.

* * * * *